United States Patent
Gharib et al.

(10) Patent No.: US 7,749,152 B2
(45) Date of Patent: Jul. 6, 2010

(54) IMPEDANCE PUMP USED IN BYPASS GRAFTS

(75) Inventors: Morteza Gharib, San Marino, CA (US); Derek Rinderknecht, Arcadia, CA (US); Idit Avrahami, Rosh-Haayin (IL); Brad Sharp, Irvine, CA (US)

(73) Assignee: California Institute of Technology, Pasadena, CA (US)

( * ) Notice: Subject to any disclaimer, the term of this patent is extended or adjusted under 35 U.S.C. 154(b) by 753 days.

(21) Appl. No.: 11/329,410

(22) Filed: Jan. 9, 2006

(65) Prior Publication Data

US 2007/0038016 A1 Feb. 15, 2007

Related U.S. Application Data

(60) Provisional application No. 60/643,915, filed on Jan. 10, 2005.

(51) Int. Cl.
*A61N 1/362* (2006.01)
(52) U.S. Cl. .......................................... 600/16
(58) Field of Classification Search ................... 600/16; 417/53
See application file for complete search history.

(56) References Cited

U.S. PATENT DOCUMENTS

| | | | |
|---|---|---|---|
| 6,254,355 B1 | 7/2001 | Gharib | |
| 6,278,847 B1 | 8/2001 | Gharib et al. | |
| 6,428,464 B1 * | 8/2002 | Bolling | 600/16 |
| 6,450,942 B1 | 9/2002 | Lapanashvili et al. | |
| 6,506,025 B1 | 1/2003 | Gharib | |
| 6,580,503 B2 | 6/2003 | Gharib et al. | |
| 6,582,208 B2 | 6/2003 | Gharib | |
| 6,608,668 B2 | 8/2003 | Gharib et al. | |
| 6,679,687 B2 | 1/2004 | Gharib | |
| 6,717,172 B2 | 4/2004 | Gharib et al. | |
| 6,956,230 B1 | 10/2005 | Gharib et al. | |
| 7,006,132 B2 | 2/2006 | Pereira et al. | |
| 7,033,132 B2 | 4/2006 | Gharib | |
| 7,163,385 B2 | 1/2007 | Gharib et al. | |
| 2001/0046445 A1 | 11/2001 | Gharib | |
| 2002/0044867 A1 | 4/2002 | Gharib | |
| 2002/0075474 A1 | 6/2002 | Gharib et al. | |
| 2002/0113963 A1 | 8/2002 | Gharib et al. | |
| 2002/0149691 A1 | 10/2002 | Pereira et al. | |
| 2002/0162956 A1 | 11/2002 | Gharib et al. | |
| 2003/0233143 A1 | 12/2003 | Gharib et al. | |
| 2004/0101414 A1 | 5/2004 | Gharib et al. | |
| 2004/0136846 A1 | 7/2004 | Gharib | |
| 2004/0151607 A1 | 8/2004 | Gharib | |
| 2004/0171904 A1 | 9/2004 | French et al. | |
| 2004/0193035 A1 | 9/2004 | Gharib | |
| 2005/0275494 A1 | 12/2005 | Gharib et al. | |
| 2005/0277865 A1 | 12/2005 | Gharib et al. | |

(Continued)

*Primary Examiner*—Carl H Layno
*Assistant Examiner*—Brian T Gedeon
(74) *Attorney, Agent, or Firm*—The Law Office of Scott C. Harris, Inc.

(57) ABSTRACT

A pump installed inside a graft in a body such as the human body to force fluid such as blood through that graft. The pump can be one which operates totally from the outside of the graft, forcing fluid through the graft without extending inside the graft. The pump can be an impedance pump, that operates based on the fluidic mismatches between the graft, and other fluid carrying vessels within the human body.

7 Claims, 1 Drawing Sheet

U.S. PATENT DOCUMENTS

2006/0195180 A1 8/2006 Kheradvar et al.
2006/0196642 A1 9/2006 Gharib et al.
2006/0209193 A1 9/2006 Pereira et al.
2006/0216173 A1 9/2006 Kheradvar et al.

* cited by examiner

IMPEDANCE PUMP USED IN BYPASS GRAFTS

CROSS REFERENCE TO RELATED APPLICATIONS

This application claims priority to U.S. Provisional Application 60/643,915, filed Jan. 10, 2005. The disclosure of the prior application is considered part of (and is incorporated by reference in) the disclosure of this application.

BACKGROUND

U.S. Pat. No. 6,254,355 describes an impedance pump which causes a pumping action that is based on fluidic impedance differences between different sections of a fluidic conduit. Basically, two or more different conduit sections have different fluidic characteristics or "fluidic impedances". The fluidic impedance is dependant on the elasticity, size and area of the conduits, among other things.

One of the conduit sections is actuated to change its inner area. The change in area causes a pressure increase in that section. The corresponding pressure increase in other sections is different because of the different fluidic characteristics of those other sections. The pressure difference causes the fluid to flow from the higher pressure area, to the lower pressure area. By continuing to change the fluidic characteristic before the system has an opportunity to return to its equilibrium state, fluid is caused to flow.

The frequency, duty cycle and timing of the pressure increase can be adjusted to change different characteristics of the fluid flow, including speed of fluid flow and direction of fluid flow. Any actuation that can reduce the inner area of a fluidic conduit can be used to actuate the pump.

SUMMARY

The present application describes an impedance pump used in cardiovascular bypass grafts.

DETAILED DESCRIPTION

The general structure and techniques, and more specific embodiments which can be used to effect different ways of carrying out the more general goals are described herein.

Blockage of arteries may be addressed during medical operations by using a graft. The graft may be a separate blood-carrying conduit, which extends in parallel with the blocked blood carrying vessel in the human body or any other body.

Figure 1:
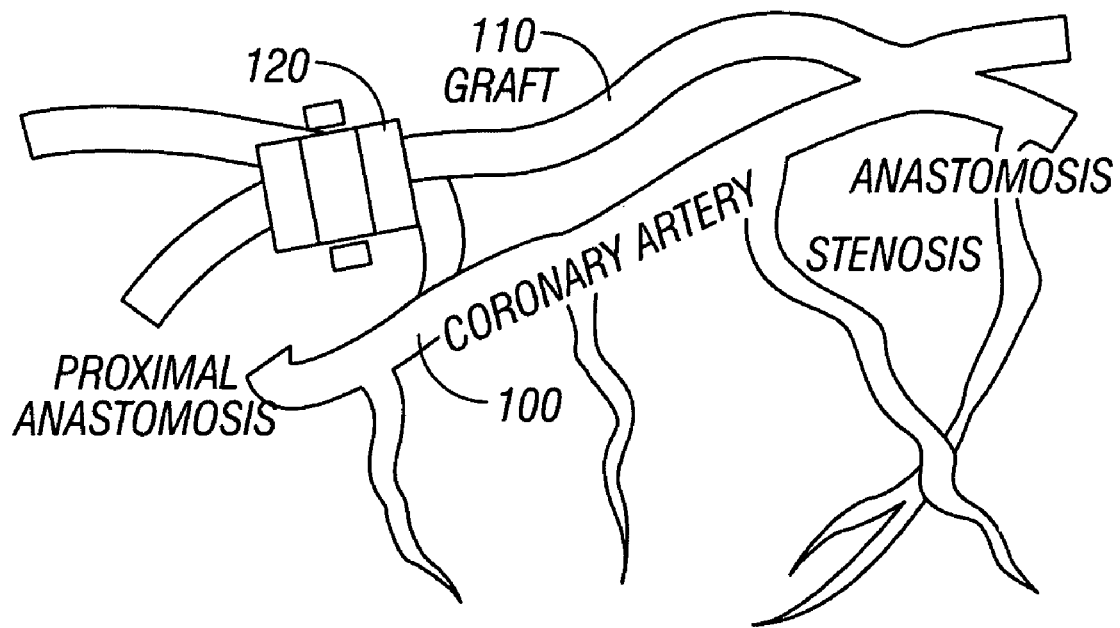
FIG. 1 shows an illustration of a coronary bypass graft with an impedance pump on the graft.
Figure 2:
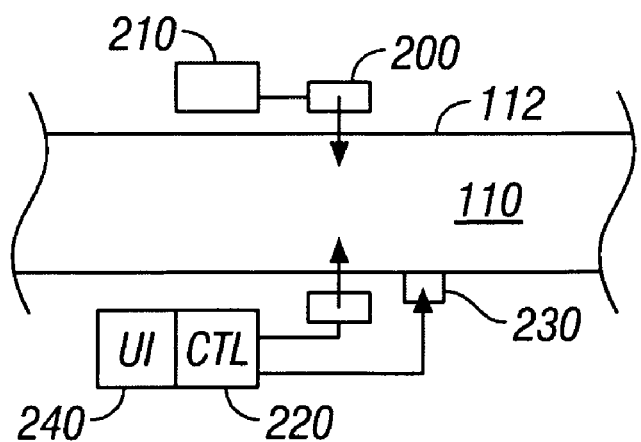
FIG. 2 shows a detailed diagram of the impedance pump assembly and controller on a conduit carrying human blood.

FIG. 1 illustrates a coronary bypass graft. The coronary artery 100 is bypassed by a graft conduit 110. In the embodiment, an impedance pump 120 is placed on the graft 110 to enhance the flow rate in the graft. This may improve the anistomosis hemodynamic and can also prevent or reduce graft occlusion, and improve patency. While the above describes a graft being used as a shunt, as an alternative, the graft can be used for other purposes, such as replacement of a diseased arterial or vein section rather than a shunt of that section.

FIG. 1 shows the impedance pump actuator 120 being implanted on a graft 110. In the embodiment, the actuator 120 forms an impedance pump, using the different fluidic characteristics of the graft 100 and the fluidic characteristics of the remaining blood conduits 100.

The actuator 120 includes a pinching portion shown as 200, located around the walls 112 of the graft 110. The pinching portion 200 is actuated to compress the walls of the pinching portion 200 towards one another, to reduce the area in the section between the walls of the pinching portion. A self-contained housing may also include an energy source shown as 210, and a controller, shown as 220, driven by the energy source. The controller may control the periodicity of the pinching, the duty cycle of the pinching to adjust the pressure increase and decrease to pump body fluid, e.g., blood, in a desired way. A non contact monitor 232 may be used to monitor the type and quantity of the flow. The controller 220 may include an interface 240, which may be a wired interface, with a wire leading outside the body, or may be a wireless interface allowing monitoring and control from the outside. For example, a controller may operate to control the speed of pinching to maintain a certain level of flow in the graft artery. The controller can be any kind of computer or microcontroller, suitably programmed, and/or controlled from programmed instructions.

Since the fluidic characteristics of the system as a whole may not be easily modeled prior to installation of the pump, it may also be highly desirable to be able to control the operation, e.g., period, duty cycle etc, of the pump after its installation.

The pincher can be any one of a number of actuation devices which cause constriction of the outer wall of the graft. The actuation devices can be, for example, any of electromagnetic, piezoelectric, ferroelectric, or electrostatic. Other techniques may also be used, including actuation of polymers, and the like.

The energy source 210 can be a battery, but power supply can also be based on patient ATP, thermal energy, or kinetic energy.

The graft 110 can be any biocompatible compliant material. The graft must be an elastic material, and is preferably near the proximal and distal most ends.

While the embodiment describes use of an impedance pump, it should be understood that other pumps may be used so long as the pumps are valveless and do not have any parts that extend within the walls forming the conduit holding blood. The impedance pump operates by exploiting the fluidic impedance mismatch between the graft and the native vessels at the anastomoses, and therefore may have special advantages, since those fluidic impedance mismatches will inherently exist. In addition, the impedance pump operates in a pulsatile manner, which may enhance the flow mixing and improve washout within the graft area.

While the above has described using the impedance pump for a coronary graft, it should be understood that the pump can be used for other grafts, including arterial, vein, artificial, or engineered tissue. It can also be used for blood vessels of any diameter in order to increase the flow within such a blood vessel.

Although only a few embodiments have been disclosed in detail above, other embodiments are possible and the inventor(s) intend these to be encompassed within this specification. The specification describes specific examples to accomplish a more general goal that may be accomplished in other way.

This disclosure is intended to be exemplary, and the claims are intended to cover any modification or alternative which might be predictable to a person having ordinary skill in the art. For example, pumping of other bodily fluids is contemplated. This device can be used in other bodies beside a human body, for example in animals, also.

Also, the inventor(s) intend that only those claims which use the words "means for" are intended to be interpreted under 35 USC 112, sixth paragraph. Moreover, no limitations from the specification are intended to be read into any claims, unless those limitations are expressly included in the claims.

What is claimed is:

1. A device comprising:
  a pump, located to pump fluid within an artificial graft which bypasses a blood carrying vessel inside a human body to enhance flow rate within the blood carrying vessel, said artificial graft connected to other blood carrying vessels inside the human body,
  said pump of a type which does not have any parts that extend within said artificial graft,
  said pump of a type that has no valves therein, and which pumps based on mismatches in fluidic impedance between said artificial graft on which the pump is attached, and said other blood carrying vessels;
  a power supply for said pump, which causes actuation of the pump to cause pumping, and
  a controller for the pump, which controls the pump to operate at a specified rate which causes a specified degree of pumping in said artificial graft.

2. A device as in claim 1, wherein said pump includes an actuator, which reduces an area of said artificial graft near said actuator, and causes a pressure increase near said area that creates a pumping effect.

3. A device as in claim 2, wherein said actuator is one of electromagnetic, piezoelectric, ferroelectric, or electrostatic.

4. A device as in claim 1, wherein said controller is wirelessly controllable.

5. A device as in claim 1, wherein said pumping comprises compressing an area of the graft periodically in a way that periodically increases the pressure in the graft, by a different amount and pressure increase than said other conduits.

6. A device as in claim 5, wherein said controller monitors the periodic pressure increase.

7. A device as in claim 5, wherein said controller monitors wirelessly from outside the body.

\* \* \* \* \*